United States Patent [19]

Mothes et al.

[11] Patent Number: 5,045,459

[45] Date of Patent: Sep. 3, 1991

[54] METHOD FOR THE PRODUCTION OF GRANULAR CITRIC ACID

[75] Inventors: Helmut A. Mothes, Granger; Bhalchandra H. Patwardhan, Elkhart, both of Ind.; Theo G. Schroeder, Wuppertal, Fed. Rep. of Germany; David J. Solow, Elkhart, Ind.

[73] Assignee: Haarmann & Reimer Corp., Springfield, N.J.

[21] Appl. No.: 594,548

[22] Filed: Oct. 5, 1990

[51] Int. Cl.$^5$ .................... C12R 1/685; C12R 1/73; C12P 7/48

[52] U.S. Cl. ................... 435/144; 435/917; 435/923

[58] Field of Search ............ 435/144, 917, 923

[56] References Cited

U.S. PATENT DOCUMENTS

| | | | |
|---|---|---|---|
| 3,936,352 | 2/1976 | Kabil | 435/144 |
| 3,966,553 | 6/1976 | Charpentier et al. | 435/144 |
| 4,178,211 | 12/1979 | Leavitt | 435/144 |
| 4,275,234 | 1/1981 | Baniel et al. | 562/584 |
| 4,278,764 | 7/1981 | Rottigni et al. | 435/144 |
| 4,389,484 | 6/1983 | Tabuchi et al. | 435/144 |
| 4,424,274 | 1/1984 | Matsumoto et al. | 435/144 |
| 4,851,573 | 7/1989 | Kulprathipania et al. | 562/580 |
| 4,910,139 | 3/1990 | Chang et al. | 435/144 |

FOREIGN PATENT DOCUMENTS

| | | |
|---|---|---|
| 0163836 | 3/1985 | European Pat. Off. |
| 0167957 | 7/1985 | European Pat. Off. |
| 186125 | 7/1986 | European Pat. Off. |
| 3502924 | 1/1985 | Fed. Rep. of Germany |
| 3808277 | 3/1988 | Fed. Rep. of Germany |

OTHER PUBLICATIONS

Chem. Abs. 01:189644(21) Lim et al.(HHKHAT) Hwahak Konghak, vol. 22 (4) pp.213-223, 1984.
Chem. Abs. 04:205486(23) Lim et al. (SMHAEH) Sanop Misaengmul Hakhoechi vol. 14(1) pp.1-8, 1986.
Biotech. Abs. 84-00300 Binot et al. (WSTED4) Water Sci. Technol. (1983) 15, 8-9, 103-15.
Biotech. Abs. 85-11283 Bailey et al. (Bibiau) Biotechnol. Bioeng. (1985) 27, 8, 1208-13.

*Primary Examiner*—Herbert J Lilling
*Attorney, Agent, or Firm*—Jerome L. Jeffers

[57] ABSTRACT

Disclosed is an improved method for preparing a particulate citric acid material. The method involves spray granulating citric acid from its partially purified fermentation broth to form granules which are freer flowing and less inclined to fracture than is citric acid prepared by crystallization techniques which properties render this material suitable for handling in bulk.

10 Claims, No Drawings

METHOD FOR THE PRODUCTION OF GRANULAR CITRIC ACID

BACKGROUND OF THE INVENTION

Citric acid is a hygroscopic organic acid used as a food acidulant, and in pharmaceutical, industrial and detergent formulations. The increased popularity of liquid detergents formulated with citric acid has been primarily responsible for the growth of this commercially valuable organic acid.

Citric acid is commercially produced by a culture fermentation process which employs molasses or a sugar such as glucose, sucrose or converted lactose as a substrate and a fungus such as *Aspergillus niger* or yeast such as *Candida lipolytica* as biocatalyst. The fermentation product typically contains biomass from the spent microorganism, carbohydrates, amino acids, proteins and salts as well as citric acid which must be separated from the fermentation broth to provide a pure product.

The literature describes many techniques for the purification of the impure fermentation broth. Among the literature references is published European Patent Application 167,957 owned by Hoechst AG which discloses a process for isolating anhydrous acidic compounds by bringing a solution of the acid into contact with a weakly basic, adsorbant, ion exchange resin, preferably those containing tertiary amino groups, and then desorbing the acid with water and/or steam.

In Offenlegungsschrift DE 3502924, owned by Benckiser GmbH, a citric acid purification process involving membrane filtration, preferably ultrafiltration, together with adsorption on a non-ionic resin such as polystyrene or polyacrylamide followed by desorption and crystallization is described.

In U.S. Pat. No. 4,851,573 there is disclosed a method for separation of citric acid from its fermentation broth by contacting the broth with a water-insoluble macroreticular gel of a weakly basic anionic exchange resin possessing tertiary amine functional groups or pyridine functional groups which resin comprises a cross-linked acrylic or styrene resin matrix. The citric acid is desorbed by water or dilute sulfuric acid.

European Patentschrift 163,836 discloses a process for the continuous preparation of granules having a narrow particle size distribution which involves spraying a slurry of the material to be granulated into a fluidized bed by means of a spraying nozzle to form granules. Fine materials escaping from the fluidized bed with the off-gas are separated and returned to the fluidized bed as nuclei for further granule formation and the granules of the desired size are formed by adjusting the sifting gas stream. The finished granules are discharged via one or more countercurrent gravity sifters installed in the inflow plate of the fluidized bed apparatus. Among the materials which are disclosed as being granulated in this manner is citric acid (Zitronensäure).

U.S. Pat. No. 4,275,234 to Baniel et al describes a method for the recovery of organic acids from their aqueous solution by an extraction process comprising a first extraction stage at which the aqueous solution is contacted with a water-immiscible extractant comprising a water-immiscible organic solvent and, dissolved therein, at least one secondary or tertiary amine in which the aggregate number of carbon atoms is at least 20 together with a back extraction stage in which the organic extract, separated from the original aqueous solution, is stripped with an aqueous liquid at a temperature which is higher by at least 20° C. than the temperature of the first extraction stage.

Other methods used to purify citric acid fermentation broths include ion exchange, nanofiltration and the so-called lime/sulfuric method, i.e. where citric acid is recovered by the addition of calcium hydroxide (lime) to form the slightly soluble tricalciumcitrate tetrahydrate. This precipitate is further purified by treating it with sulfuric acid to yield calcium sulfate (gypsum) and a solution of free acid.

Regardless of the preliminary purification steps used in the manufacture of citric acid, the final step in its production typically includes a series of crystallization steps involving evaporation, crystallization and centrifugation equipment. A conventional crystallization scheme consists of a batch vacuum-pan evaporator or a forced circulating evaporator coupled with auxiliary tankage and appropriate centrifuge equipment. Within these systems the crystals formed are separated from the mother liquor and advanced to the next crystallization step which can be carried out in a batchwise or continuous operation.

SUMMARY OF THE INVENTION

The present invention is a method for the production of citric acid granules which involves producing a citric acid containing fermentation broth by the fermentation of an appropriate carbon/hydrogen source as substrate in the presence of a suitable microorganism. After separation of the biomass residue of the microorganism, which procedure will typically leave at least about 2% (w/w) based on the amount of citric acid of unreacted substrate, the fermentation broth is injected into the chamber of a fluidized bed device where it is brought into contact with a suitable seed material to thereby form granules of citric acid by suspending the injected material in a flow of upwardly moving air. These granules have been found to have improved bulk handling characteristics as compared to particulate citric acid prepared by crystallization techniques. Upon further purification, such as by ultrafiltration, citric acid granules which dissolve in water to provide a clear solution, and are, therefore suitable for beverage purposes are provided. Spray granulation of the fermentation broth which has been subjected to further purification steps, provides granules which have the improved flow characteristics and which, when prepared from a sufficiently purified fermentation broth, also qualify as USP grade.

DESCRIPTION OF THE INVENTION

Citric acid is typically produced by the fermentation of a suitable substrate as source of carbon and hydrogen such as glucose, sucrose, lactose, molasses or paraffin. A microorganism, such as an appropriate strain of a fungus of the species *Aspergillus niger* causes the fermentation to proceed by catabolism of the substrate to citric acid. This process results in the formation of a crude fermentation broth containing citric acid along with copious impurities including biomass derived from the spent fungus. Typically, this fermentation broth is purified by a multi-step process including crystallization to provide the final product. Crystallization has the drawback of added cost and problems with residual mother liquors which must be recycled or further purified. In addition, the crystallized material also tends to fracture, resulting in fines. At present, citric acid is not sold commercially in bulk. More significantly, the crystallized material tends to cake and to exhibit poor flow characteristics in terms of caking and fracturing. Presently, all citric acid of commerce is packed in small containers of 1 ton or less with some type of moisture barrier. All bulk conveying units are minimized in dealing with citric acid because of the ease with which its crystals are fractured. It has now been discovered that these bulk handling difficulties can be alleviated by recovering the citric acid content of the fermentation broth by spray granulation techniques. While citric acid cannot be successfully spray dried, it has been discovered that a citric acid product with excellent bulk handling properties can be obtained by spray granulation regardless of the state of purity of the citric acid stream being used.

The initial step in this process involves purifying the crude fermentation broth to substantially remove the biomass therefrom. The separation step, which must remove enough biomass to permit the filtered broth to pass through the spray nozzles in the subsequent spray granulation step, is accomplished by the use of conventional means such as vacuum drum filters or belt discharge filters. Centrifugation with decantation can also be used to remove the mycelium. The filtration step does not remove impurities such as proteins and carbohydrates or unreacted substrate which will remain in the filtrate in amounts of from 2% to 30% (typically from 5% to 10%) w/w based on the amount of citric acid.

Decationization of the partially purified citric acid containing fermentation broth is desirable, especially when the spray qranulation step is to be carried out at a relatively high temperature. Suitable ion exchange resins for this step include Amberlite 200 from Rohm & Haas, Duolite C-291 from Dow Chemical Co. and Lewatit SP-112 from Bayer AG.

The filtered or centrifuged citric acid containing material, which contains at least about 2% w/w unreacted substrate based on the weight of the citric acid in solution and preferably contains from 50% to 75% w/w citric acid, is introduced into the chamber of a fluidized bed reactor and suspended therein along with seed particles which may consist of citric acid or other suitable seed material. The amount of unreacted substrate may be as high as about 30% (w/w). Significantly higher amounts will make spray granulation difficult due to excessive agglomeration of the citric acid. Citric acid, either crystallized or spray granulated, can be used as the seed material. Alternatively, other materials, particularly malic and/or fumaric acid, as well as sweeteners such as Aspertame ® can be used as the seed material or combined with the citric acid solution used in the spray granulation procedure to provide blended citric acid containing granules. Typically, the seed particles are spherical in shape and will range in size from 50 to 1,000 microns in diameter. Temperature and pressure conditions are not critical to the success of this operation provided that water evaporation and granule formation take place. The process is carried out until the citric acid granules have grown to the desired size, typically 300 to 2,000 microns in diameter.

Further purification of the fermentation broth by ultrafiltration, again without crystallization, provides, upon spray granulation, a citric acid product that yields a crystal clear solution when dissolved in water. Accordingly, such a product is suitable for food use where color is not important such as is the case with many beverages. The ultrafiltration step, using a membrane that will remove all solutes having a molecular weight greater than about 1,000 Daltons, is carried out by conventional means.

Ultrafiltration is a purification/concentration process whereby a liquid is circulated under pressure across a permeable selective membrane. Solvent and low molecular weight species are transported through the membrane while retaining higher molecular weight species in the recirculating liquid. Filtering with a membrane having a cut off of 1,000 Daltons will still leave unreacted substrate and other impurities in the filtrate. Unreacted substrate can be further reduced by nano-filtration to remove solutes with molecular weights above about 250 Daltons.

When a citric acid product qualifying as United States Pharmacopia (U.S.P.) and Food Chemicals Codex (F.C.C.) is desired, the fermentation broth is subjected to further purification measures such as the lime/sulfuric method or the solvent extraction procedure disclosed in previously mentioned U.S. Pat. No. 4,275,234. In general, this procedure involves contacting two immiscible liquids which have different affinities for a selected solute, thereby transferring this solute into one phase, and then separating the two phases. The affinity between solute and solvent can be altered by changing the temperature, pH or other variable In the process described in U.S. Pat. No. 4,275,234 an aqueous citric acid solution is contacted with a water immiscible extractant comprising a water immiscible organic solvent and, dissolved therein, at least one secondary or tertiary amine in which the aggregate number of carbon atoms is at least 20 combined with a back-extraction in which the organic extract, separated from the original aqueous solution, is stripped with an aqueous liquid at a temperature which is higher by at least 20° C. than the temperature of the first extraction stage. The recovered citric acid fermentation broth is then spray granulated as before. It is important that if the citric acid containing broth is subjected to crystallization during any step of the process it be redissolved and spray granulated since direct crystallization results in crystals which tend to bind together and have poor flow characteristics as opposed to those which are prepared by spray granulation which have been found to flow freely during bulk handling.

The method of practicing the present invention is further illustrated by the following examples where the dryer used was a Uni-Glatt laboratory model fluid bed dryer with variable air temperature and flow through the bed. The device has a 6 inch Wurster insert which consists of a container (5 ½" diameter by 6 ½" height) for the seed particles that fits against the bottom of the device's expansion chamber. The plate on the bottom of the Wurster has holes in it to distribute the air through the bed with the holes in the center being of a larger diameter than the rest of the holes in the plate. A cylindrical hollow tube (2 ¾" diameter by 6" length) called a partition is suspended above these larger diameter holes creating a higher air flow up through the partition than up around the outside of the partition. The air flow is adjusted based on the quantity and density of the seed particles so that the particles flow up inside the partition into the expansion chamber and then fall back down outside the partition into the area with less air flow while the bed is kept fluidizing and drying. This difference in air flow creates a circular upward and downward movement of the particles. The spray nozzle is installed at the bottom of the partition pointed upwards.

This arrangement keeps the atomized liquid co-current with the motion of the seed particles being coated and results in a smooth, continuous formation of the citric acid granules. The speed of the circular flowing motion of the seed particles is adjustable by regulating the amount of air going through and that going outside the partition.

The height of the Wurster insert partition is adjustable vertically and was adjusted from $\frac{1}{4}''$ to $\frac{3}{4}''$ up from the bottom plate. When denser seed particles are used, up to $\frac{3}{4}$ of the holes outside the partition are blocked off to provide a higher linear velocity for the air to lift the particles up through the inside of the partition and maintain a smooth circulation of material through the spraying area. The total air flow was adjusted to get a good flow of seed particles through the partition and keep the bed outside the partition fluidized. Typical operating temperatures during the granulation process are 50° C. to 150° C. although a temperature of from about 80° to 120° C. is preferred when fermentation broth which has not been nanofiltered is used. This is the case because this material contains unfermented sugars which will melt at higher temperatures thereby complicating the spray granulation procedure. Feed rate varied from 3 ml/minute to 15 ml/minute. Atomization air pressure ranged from 1 to 4 bar. When citric acid granules of a preselected, uniform size are desired, the device described in DE 3,808,277 can be used. This device is capable of generating the seed particles in situ since some of the feed droplets are converted into seed material by evaporation and drying thereby eliminating or reducing the requirement for externally added seed material.

EXAMPLE I

A crude fermentor beer containing citric acid (15% w/w) was prepared in a one cubic meter agitated fermentor. Glucose, prepared by the enzymatic conversion of corn starch, was diluted to 20% w/v in a trace element solution, sterilized and inoculated with spores of *A. niger*. After incubation for 5 days with aeration (1 vvm), most of the fermentable sugar was converted to citric acid and the fermentation was terminated.

This material was filtered using a pressure filter to remove substantially all of the biomass and decationized by passing the filtrate through a strong acid cation exchange resin, i.e. Duolite C-291 from Dow to remove sodium, potassium, magnesium, ammonium and other undesirable cations. The resultant was vacuum concentrated in a laboratory rotovap at 60° C. to 68% w/w citric acid and about 5% unfermented sugar. The concentrated solution was atomized into the Uni-Glatt film coater equipped with a Wurster column as previously described to form a fluidized bed in which citric acid particles formed as the water evaporated. During the process of spray granulation, citric acid seed crystals of approximately 200 microns in diameter were suspended by a stream of hot air (110° C.) in the column. As the citric acid solution is atomized into the bed, a thin film of liquid coats each seed particle and rapidly dries on the surface thereof forming successive layers like an onion. The drying rate controlled by the bed temperature and humidity must be such as to allow for the surface drying to occur before wet particles collide and dry together in an agglomeration process. In this experiment, the bed temperature and relative humidity were 85° C. and 5% respectively. The particles were allowed to grow in size to an average diameter of 800 microns at which time the run was completed. Using a seed particle of 200 microns in diameter and increasing the diameter to 800 microns allows the process to achieve good capacity. The spray granulated citric acid particles were found to be spherical in shape with slight irregularities. Close examination of the granules revealed that the citric acid was in the form of a series of crystalline layers. This is in contrast to an agglomeration process in which two or more seed particles clump together to form very irregular shapes with weak attachments. These particles are usually soft and fragile as compared to true granules.

These citric acid granules were found to be superior to particulate citric acid prepared by crystallization in which a citric acid solution was evaporated to 75% w/w at 60° C. to exceed saturation to provide citric acid crystals, which were recovered by centrifugation, washed with water and air dried in hot air, both in terms of reduced caking and improved bulk handling properties. These improved properties were determined as follows:

A. Cake Tests:

i. Samples of spray granulated citric acid and crystallized citric acid prepared as described in this example were stored in a controlled atmosphere at 70% relative humidity and 80° F. in an open container for 72 hours. Upon examination, the spray granulated material exhibited no caking whereas the crystalline citric acid exhibited slight to moderate caking.

ii. A 50 lb. sample of spray granulated citric acid was stored in a standard double walled paper bag with a polyliner from March to September in a warehouse without air conditioning in Elkhart, Indiana USA. No caking was observed at the end of this period. Crystallized citric acid often cakes under these conditions.

B. Particle Hardness and Attrition:

Bulk particle hardness was tested using an Instron hardness tester Model 1000. An average of four trials gave a hardness ratio of 0.78 comparing the spray granulated material of this experiment with the crystallized material representing a significant difference in particle hardness.

Attrition tests were conducted by injecting 5 lb. samples of spray granulated and crystallized citric acid into a device which carried it through a chamber designed to simulate bulk handling conditions in a stream of flowing air at a controlled velocity. The spray granulated material was found to withstand these test conditions with 3 to 4 fold less particle attrition than did the crystallized material providing the advantage of significantly reducing the amount of fines produced during normal bulk handling.

The spray granulated citric acid used in the bulk hardness, attrition and long term caking studies was spray granulated using the device described in DE 3,808,277.

EXAMPLE II

Citric acid granules were prepared as in the previous example except that further purification was achieved by circulating the decationized fermentation beer in a closed loop through a 4" spiral ultrafiltration membrane having a nominal cut off of 1,000 Daltons. This process was continued until 99.5% of the citric acid had permeated retaining the higher molecular weight impurities such as carbohydrates and proteins were removed. The resultant permeate was granulated as previously described to provide a product which was similar in appearance to that prepared in example 1 whose properties are:

Bulk Density: 700-850 grams/1
color: Light Tan
Size: 600-1200 Microns
Shape: Spherical, slightly irregular These granules formed a crystal clear solution when dissolved in water to provide a 50% w/w solution whereas those granules prepared by the procedure of example 1 provided a cloudy solution under similar conditions.

EXAMPLE III a. Citric acid granules were prepared as described in the above example except that after ultrafiltration the fermentation broth was subjected to liquid-liquid extraction accomplished by:

Decationized fermentor beer, 20 liters, containing 13.8% w/v citric acid was contacted at room temperature with 20 liters of solvent of the following composition:

| Component | % w/v |
| --- | --- |
| Trilaurylamine | 34.0 |
| Dilaurylamine | 0.5 |
| Petroleum Fraction | |
| Boiling at 180-210° C. | 60.5 |
| 1-N-Octanol | 5.0 |

After separation of the fractions, the solvent was recontacted with 20 liters of fresh beer mixed, settled and again separated. Citric acid, 1630 grams, was extracted into the solvent. The solvent was washed at 55° C. with 1 liter of water to remove entrapped beer droplets and separated again. In this procedure, 218 grams of citric acid were back extracted. The solvent was then extracted with 4 liters of water at a temperature ranging from 80°-97° C. This process was repeated to yield 1.22 kg citric acid in 8 liters.

After treating with carbon and evaporating to 50% w/w, this material was coated onto U.S.P. citric acid seed.

The purified broth was introduced into the spray granulator as before without having been subjected to a crystallization step. The granulation process provided citric acid particles having bulk handling properties as previously described and the material which had a final composition of 12% w/w seed and 88% from the coating solution was found to be sufficiently pure to be classified as U.S.P. This degree of purity was determined following the assay described in Pharmacopeia of the United States, XXII Edition, page 315 and Food Chemicals Codex, Third Edition (1981), Pg. 86-87.

EXAMPLE IV

A fermentation was conducted as previously described except that molasses was used as the substrate. The fermentation product was filtered to remove biomass and evaporated to provide a product containing 35% solids which was spray granulated in the Uni-Glatt granulator at a feed rate of 5 ml/minute and outlet temperature of 85° C. The granules produced had properties similar to those previously described using dextrose as the substrate except that they were darker in color and slightly less uniform in size.

EXAMPLE V

Attempts to spray dry citric acid revealed that a successful operation could not be achieved without disturbances due to massive wall deposition.

The conditions and test procedures were:

| Dryer Type: | Nubilosa, 2-fluid nozzle |
| --- | --- |
| Feed: | Aqueous solution of purified citric acid, room temperature, saturation concentration of 60% |
| Drying Parameters: | Nitrogen, inlet temperature 140° C., exhaust temperature 70° C. |
| Results: | Almost all of the sprayed product stuck to the walls forming a glossy, dense layer. Despite variation of the drying parameters, this phenomenon could not be avoided |

What is claimed is:

1. In combination with the method for the production of citric acid which comprises the fermentation of an appropriate carbon and hydrogen source as substrate in the presence of an appropriate microorganism to produce a fermentation broth containing citric acid together with impurities including the biomass residue of the microorganism, the improvement which comprises treating the fermentation broth to substantially remove the biomass and thereby provide a partially purified product containing citric acid and from about 2% to 30% (w/w) unreacted substrate and other impurities based on the weight of citric acid and introducing this product, without further purification, into the chamber of a fluidized bed reactor where it is suspended in a flow of upwardly rising air together with seed particles to thereby form granules of citric acid.

2. The method of claim 1 wherein the partially purified product contains from 5 to 10% unreacted substrate and other impurities.

3. The method of claim 1 wherein the treated product contains from 50 to 75% (w/w) citric acid.

4. The method of claim 1 wherein the seed particles are externally added, are spherical in shape and range in size from 50 to 1,000 microns in diameter.

5. The method of claim 1 wherein the citric acid granules are allowed to grow to a size of from 300 to 2,000 microns in their longest dimension.

6. The method of claim 1 wherein the air entering the fluidized bed reactor is at a temperature of 50 to 150° C.

7. The method as in any one of claims 1-6 wherein the fermentation broth is passed through a filtering apparatus to remove particles larger than 1,000 Daltons after the separation of the biomass.

8. The method of claim 7 wherein the filtering apparatus removes material greater than 250 Daltons.

9. The method of claim 1 wherein the seed particles are comprised of citric acid, malic acid or fumaric acid.

10. The method of claim 1 wherein malic or fumaric acid is added to the fermentation broth before its introduction into the fluidized bed reactor.

* * * * *